US009717404B1

(12) United States Patent
Brauner et al.

(10) Patent No.: US 9,717,404 B1
(45) Date of Patent: Aug. 1, 2017

(54) MULTIFOCAL LENS AND SYSTEM AND METHOD FOR SIMULATING THE SAME

(71) Applicant: SPECIALEYES, LLC, Bradenton, FL (US)

(72) Inventors: Stephen Edward Brauner, Bradenton, FL (US); Michael John Simpson, Arlington, TX (US)

(73) Assignee: SPECIALEYES, LLC, Bradenton, FL (US)

( * ) Notice: Subject to any disclaimer, the term of this patent is extended or adjusted under 35 U.S.C. 154(b) by 180 days.

(21) Appl. No.: 14/600,543

(22) Filed: Jan. 20, 2015

(51) Int. Cl.
| | |
|---|---|
| *A61B 3/02* | (2006.01) |
| *G02C 7/00* | (2006.01) |
| *A61B 3/00* | (2006.01) |
| *A61B 3/032* | (2006.01) |
| *A61B 3/09* | (2006.01) |
| *G02C 7/02* | (2006.01) |
| *G02C 7/06* | (2006.01) |
| *G02C 7/04* | (2006.01) |
| *A61B 3/028* | (2006.01) |
| *A61F 2/16* | (2006.01) |

(52) U.S. Cl.
CPC ............ *A61B 3/0025* (2013.01); *A61B 3/028* (2013.01); *A61B 3/032* (2013.01); *A61B 3/09* (2013.01); *A61F 2/1618* (2013.01); *G02C 7/02* (2013.01); *G02C 7/027* (2013.01); *G02C 7/028* (2013.01); *G02C 7/041* (2013.01); *G02C 7/044* (2013.01); *G02C 7/045* (2013.01); *G02C 7/06* (2013.01); *A61B 3/0041* (2013.01); *A61F 2/1613* (2013.01); *G02C 2202/20* (2013.01)

(58) Field of Classification Search
CPC ... A61B 3/0025; A61B 3/0032; A61B 3/0033; A61B 3/0041; A61B 3/028; A61B 3/032; A61B 3/10; A61B 3/111; G02C 7/00; G02C 7/02; G02C 7/028; G02C 7/027; G02C 7/041; G02C 7/044; G02C 7/045; G02C 2202/20; G02C 2202/22; G02C 7/04; G02C 7/047; G02C 13/005; A61F 2/1613; A61F 2/1618; A61F 2/1654
USPC .............. 351/159.05, 159.1, 159.11, 159.12, 351/159.14, 159.15, 159.41, 159.43, 351/159.44, 205, 210, 221, 239, 246
See application file for complete search history.

(56) References Cited

U.S. PATENT DOCUMENTS

| | | | | |
|---|---|---|---|---|
| 3,472,581 A | * | 10/1969 | Bronstein | ............... G02C 7/042 351/159.41 |
| 3,614,218 A | * | 10/1971 | Bronstein | ............... G02C 7/042 351/159.41 |
| 5,493,350 A | * | 2/1996 | Seidner | ............ B29D 11/00086 351/159.47 |
| 5,526,071 A | * | 6/1996 | Seidner | ............ B29D 11/00086 351/159.41 |

(Continued)

*Primary Examiner* — Loha Ben
(74) *Attorney, Agent, or Firm* — Foley & Lardner LLP

(57) ABSTRACT

An apparatus for generating simulated images includes an input device, a processor and a display device. The input device is configured to input information on a pupil of an eye and design information for a multifocal lens. The processor is configured to generate, based on the inputted pupil information and design information, a simulated image that is visible to the eye when the multifocal lens is disposed in the eye. The display device is configured to display the simulated image generated by the processor.

28 Claims, 10 Drawing Sheets

(56) References Cited

U.S. PATENT DOCUMENTS

| | | | | |
|---|---|---|---|---|
| 5,677,750 A * | 10/1997 | Qi | ............................ | G09B 23/28 |
| | | | | 351/205 |
| 6,007,201 A * | 12/1999 | Wada | ...................... | B29C 33/42 |
| | | | | 351/159.41 |
| 6,030,077 A * | 2/2000 | Sawano | ................. | A61F 2/1618 |
| | | | | 351/159.42 |
| 6,142,625 A * | 11/2000 | Sawano | ................. | G02C 7/042 |
| | | | | 351/159.07 |
| 6,260,966 B1 * | 7/2001 | Sawano | ................. | A61F 2/1618 |
| | | | | 351/159.43 |
| 6,957,891 B2 * | 10/2005 | Fiala | ...................... | G02C 7/028 |
| | | | | 351/159.02 |
| 7,009,713 B2 * | 3/2006 | Seko | ........................ | G01B 9/02 |
| | | | | 356/498 |
| 7,188,949 B2 * | 3/2007 | Bandhauer | ............. | A61F 2/1613 |
| | | | | 351/159.41 |
| 7,775,663 B2 * | 8/2010 | Andino | ................. | A61B 3/0025 |
| | | | | 351/212 |
| 7,780,293 B2 * | 8/2010 | Andino | ................. | A61B 3/0025 |
| | | | | 351/212 |
| 8,079,704 B2 * | 12/2011 | Sanger | .................. | A61F 2/1618 |
| | | | | 351/159.42 |
| 8,083,346 B2 * | 12/2011 | Legerton | ................... | G02C 7/04 |
| | | | | 351/159.14 |
| 8,157,374 B2 * | 4/2012 | Bandhauer | ............ | A61F 2/1618 |
| | | | | 351/159.53 |
| 8,506,075 B2 * | 8/2013 | Bandhauer | ............ | A61F 2/1618 |
| | | | | 351/159.11 |
| 8,556,416 B2 * | 10/2013 | Lawu | ................... | G02B 5/1895 |
| | | | | 351/159.15 |
| 9,211,061 B2 * | 12/2015 | Kasthurirangan | ..... | A61B 3/032 |

* cited by examiner

MULTIFOCAL LENS AND SYSTEM AND METHOD FOR SIMULATING THE SAME

TECHNICAL FIELD

The present inventive concept relates to multifocal lenses, and systems and methods for simulating the multifocal lenses and generating simulated images.

BACKGROUND

Multifocal lenses are designed to provide different lens powers, e.g., near vision and distance vision, for a person wearing the lenses. Contact lenses are routinely used by presbyopic patients who can no longer accommodate fully. One approach to the correction of presbyopia is to use simultaneous vision lenses. Compared to bifocal and progressive lenses which require the eye to select, e.g., by shifting upward or downward, different zones of a spectacle lens used to view near or far objects, the simultaneous vision lenses allow the eye to view near or far objects through multiple powers, e.g., both distance and near powers, at the same time across the pupil. That is, the simultaneous vision lenses allow the presbyopic patients to select a correct power choice across the pupil depending on how close or far the objects are.

Meanwhile, in manufacturing custom lenses, systems and methods for designing a lens can be utilized. Methods for calculating image properties are known, and these have been used for both monofocal and multifocal lenses. These can be used to evaluate general properties for a specific design. For a multifocal contact lens design to be customized for an individual patient, however, there is a need to thoroughly evaluate the imaging performance of the individual patient over a number of optical design variables, such as a range of object distances, a range of pupil diameters and the amplitude of accommodation. The clinical consequence of presbyopia may be represented in terms of such design variables. For example, as a person becomes more presbyopic, the person is not able to view an object at a customary working distance without experiencing visual symptoms; an increased pupil size may result in reduction in the range of clear near vision in dim light; and the amplitude of accommodation may be insufficient to meet the near vision demands of the person. Moreover, with presbyopia, the accommodative power of the eye declines over a period of years. Therefore, the presbyopic patients will need different add powers as presbyopia progresses and there is a need for reassessing the lens design periodically.

Many multifocal contact lenses do not correct for the astigmatism of the eye, which can degrade both monofocal and multifocal vision. A customized multifocal contact lens will also have astigmatism corrected, if appropriate.

Therefore, to take the appropriate information and use it to change the lens design for an individual patient, there is a need for identifying design variables that are clinically important for correcting presbyopia and utilizing those design variables to simulate images for both the near vision and distance vision to optimize clinical implementation of custom lenses for the individual patient.

Furthermore, it is recognized that as technology advances, different types of custom lens designs may be developed. Accordingly, there is a need for custom lens design systems and methods that can easily support new types of custom lens designs.

SUMMARY

Multifocal contact lenses may have a center region, an outer region, and an intermediate region that is disposed between the center region and the outer region and has an annular region. Embodiments of the present disclosure are directed to systems and methods for simulating the multifocal lenses and generating simulated images to provide improved simulated image contrast for both near vision and distance vision and enhanced support for different types of multifocal lens designs. The refractive error of the eye is corrected by the underlying spherical and cylindrical corrections of the contact lens, and the multifocal component, and the effect that it has over a range of objects distances, is evaluated.

One embodiment relates to an apparatus for generating simulated images, including an input device, a processor and a display device. The input device is configured to input information on a pupil of an eye and design information for a multifocal lens. The processor is configured to generate, based on the inputted pupil information and design information, a simulated image that is visible to the eye when the multifocal lens is disposed in the eye. The display device is configured to display the simulated image generated by the processor.

The simulated image may include a first simulated image relating to a first defocus value indicating distance vision of the eye, a second simulated image relating to a second defocus value indicating intermediate vision of the eye, and a third simulated image relating to a third defocus value indicating near vision of the eye. The display device may be configured to display the first, second and third simulated images side by side.

The pupil information may include a diameter of the pupil of the eye, and the design information may include at least one of add power and physical dimensions of regions of the multifocal lens.

The apparatus may further include a means to input aberration to an eye model.

The multifocal lens may be a contact lens.

The processor may be further configured to input aberrations for the eye based on measured wavefront aberrations or aberrations estimated from a corneal topography. A total phase map may be calculated by summing an eye phase map and a multifocal phase map in the multifocal lens. The processor may be further configured to calculate a point spread function (PSF) based on the total phase map and a particular defocus value, and generate a simulated image relating to the particular defocus value based on the calculated PSF.

The display may be configured to update the simulated image after one of the information on the pupil and the design information changes.

The processor may be configured to generate a plurality of images corresponding to predetermined sets of values of input parameters relating to the pupil information and the design information. The input device may be configured to input a particular set of values of the input parameters. When the particular set of values of the input parameters is inputted, the processor may be configured to look up the plurality of images and the display may be configured to update the simulated image by displaying an image, among the plurality of images, corresponding to the particular set of values of the input parameters.

The input device may be configured to input a particular set of values of input parameters relating to the pupil information and the design information, and when the particular set of values of the input parameters is inputted, the processor may be configured to generate the simulated image corresponding to the particular set of values of the input parameters.

Another embodiment relates to a method for generating simulated images. According to the method, information on a pupil of an eye and design information for a multifocal lens is inputted by an input device. Based on the inputted pupil information and design information, a simulated image that is visible to the eye when the multifocal lens is disposed in the eye, is generated by a processor. The simulated image generated by the processor is displayed by a display device.

In generating the simulated image, a first simulated image relating to a first defocus value indicating distance vision of the eye, a second simulated image relating to a second defocus value indicating intermediate vision of the eye, and a third simulated image relating to a third defocus value indicating near vision of the eye, may be generated. In displaying the simulated image, the first, second and third simulated images may be displayed side by side.

The pupil information may include a diameter of the pupil of the eye, and the design information may include at least one of add power and physical dimensions of regions of the multifocal lens.

The multifocal lens may be a contact lens.

In generating the simulated image, aberrations for the eye may be inputted using measured wavefront aberrations, or aberrations estimated from the corneal topography. A total phase map may be calculated by summing an eye phase map and a multifocal phase map in the multifocal lens. A point spread function (PSF) may be calculated based on the total phase map and a particular defocus value, and a simulated image relating to the particular defocus value may be calculated based on the calculated PSF.

In displaying the simulated image, the simulated image may be updated after one of the information on the pupil and the design information changes.

In generating the simulated image, a plurality of images corresponding to predetermined sets of values of input parameters relating to the pupil information and the design information may be generated. In inputting the information, a particular set of values of the input parameters may be inputted. In displaying the simulated image, when the particular set of values of the input parameters is inputted, the plurality of images may be looked up and the simulated image may be updated by displaying an image, among the plurality of images, corresponding to the particular set of values of the input parameters.

In inputting the information, a particular set of values of input parameters relating to the pupil information and the design information may be inputted. In generating the simulated image, when the particular set of values of the input parameters is inputted, the simulated image corresponding to the particular set of values of the input parameters may be generated.

Still another embodiment relates to a computer readable storage medium storing instructions that when executed by a processor, cause the processor to perform operations for generating simulated images. The operations includes inputting, by an input device, information on a pupil of an eye and design information for a multifocal lens, based on the inputted pupil information and design information, generating, by the processor, a simulated image that is visible to the eye when the multifocal lens is disposed in the eye, and displaying, by a display device, the simulated image generated by the processor.

Still another embodiment relates to a multifocal lens, where one lens surface has a center region, an outer region and an intermediate region. The center region has a radius of curvature R1. The outer region has a radius of curvature R3. The intermediate region has a radius of curvature R2 and is disposed between the center region and the outer region. The intermediate region is an annular region. The radius of curvature R2 is different from the radius of curvature R1 or the radius of curvature R3.

The multifocal lens may be a contact lens.

The annular region may have a circular arc that blends tangentially with both the center region and the outer region.

The circular arc may be a portion of an off-axis circle that does not have its center on an optical axis of the multifocal lens.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Exemplary embodiments will now be described in detail with reference to the accompanying drawings.

Figure 1:
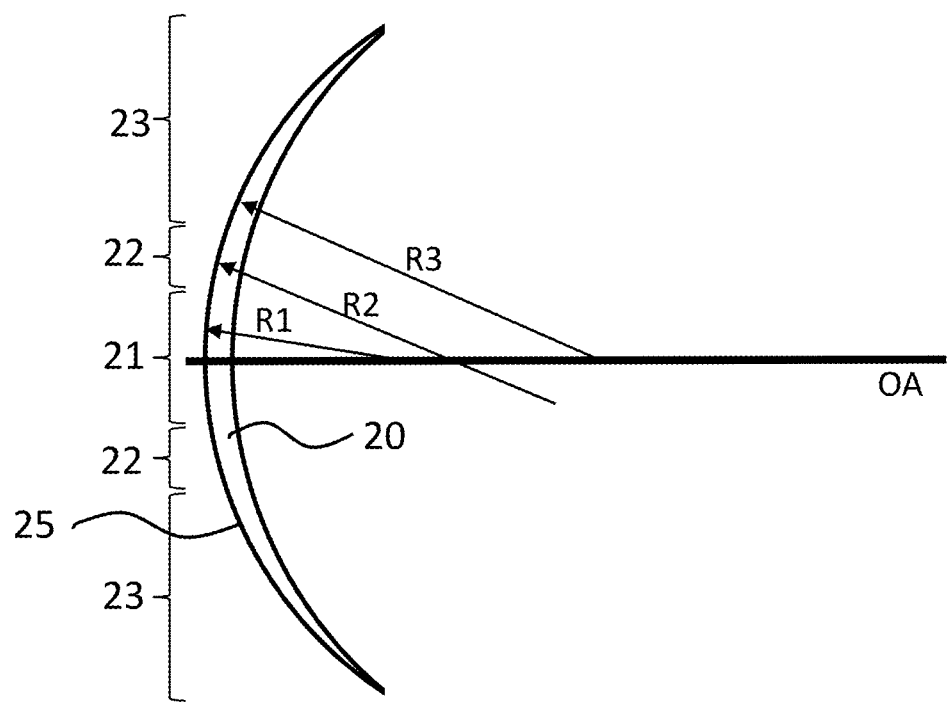
FIG. 1 is a diagram showing an exemplary design of a multifocal lens in accordance with a first embodiment.

FIG. 1 is a diagram showing an exemplary surface profile of an example design of a multifocal lens 20 in accordance with the first embodiment. The multifocal lens 20 according to this embodiment is a multifocal contact lens that has three zonal regions and an anterior lens surface. For example, the multifocal contact lens includes an anterior lens surface 25 that has a center region 21 (or zone) with a radius of curvature R1, an intermediate region 22 (or zone) with a radius of curvature R2, and an outer region 23 (or peripheral zone) with a radius of curvature R3. Here, the radius of curvature R2 is different from the radius of curvature R1 or the radius of curvature R3. The radii of curvature R1, R2 and R3 may be different from each other. The lens may have a diameter of 14 mm but the present inventive concept is not limited thereto. The multifocal lens 20 may be multifocal lenses other than contact lenses, which may include, for example, a multifocal intraocular lens (IOL) that is routinely implanted in patients' eyes to treat cataracts or myopia.

Figure 2A:
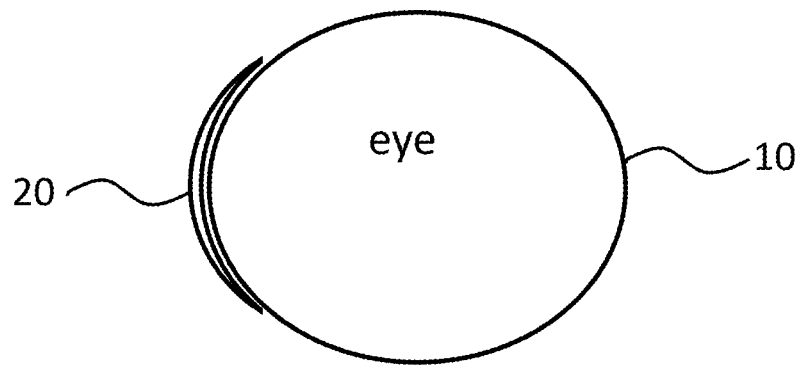
FIGS. 2A and 2B are diagrams showing alternative representations of an exemplary design of optical components of a contact lens.
Figure 2B:
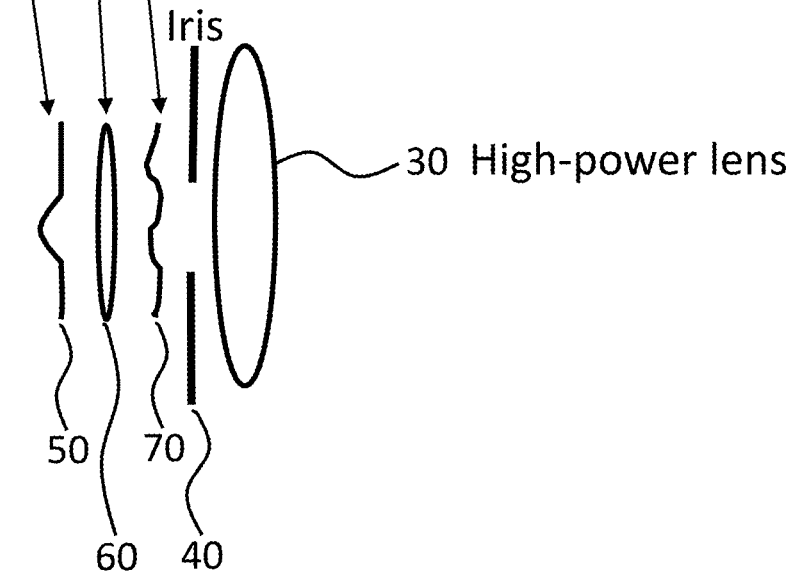

Contact lenses have very strong surface curvature in order to conform to the cornea, which provides most of the power of the eye. For example, contact lenses may have a radius of curvature of approximately 8 mm. The additional optical effects that are provided by the contact lens can be revealed by removing the highly curved substrate material that primarily acts to support the optical components. This is illustrated in FIGS. 2A and 2B, where the optical properties of an eye 10 and the multifocal lens 20 may be simulated using thin lenses placed in front of a high-power lens or a perfect lens 30 with the power of the eye. The high-power lens 30 simulates the eye itself and may include the spherical and cylindrical corrections provided by a basic contact lens. The thin lens components may include a multifocal component 50, a defocus component 60 and an aberration component 70 that simulates the aberration of an eye. A phase map may be calculated or otherwise obtained for each optical component. The iris 40 can include or exclude light, independently of the phase map.

Figure 3B:
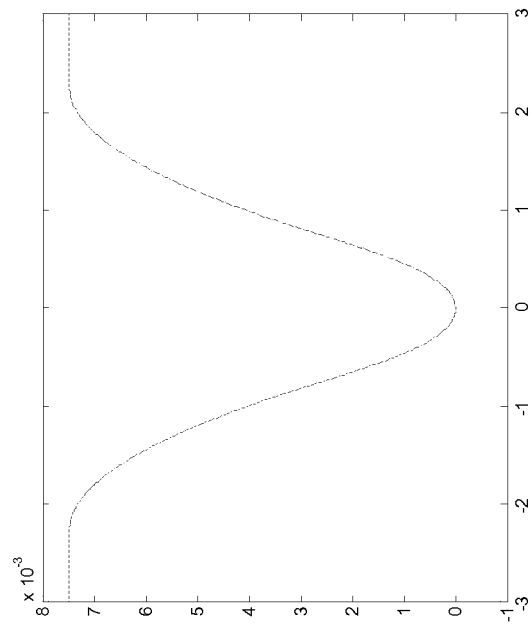
FIGS. 3A and 3B show a simplification of the optical components.
Figure 3A:
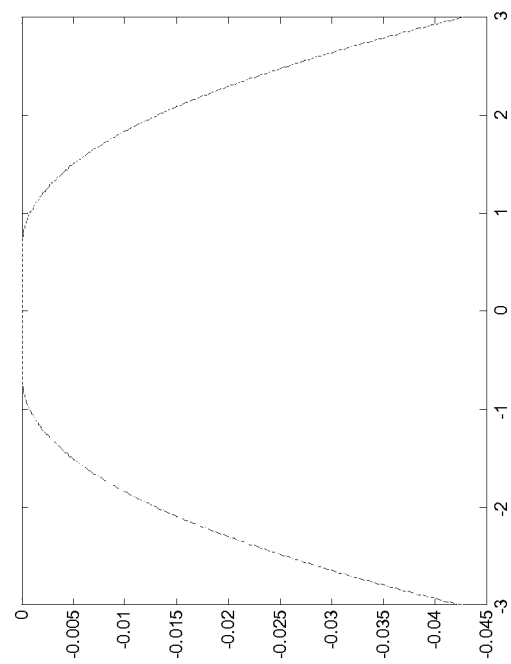

FIG. 3A shows a simplified representation of the optical properties of the multifocal design as a thin lens, i.e., an exemplary surface profile of an example design of the multifocal lens 20, where the radius of curvature R1 of the center region 21 of the physical surface profile of the multifocal lens 20 has been subtracted from the entire surface profile. FIG. 3B shows an alternative representation of the optical properties of the same multifocal design, where the radius of curvature R3 of the outer region 23 has been subtracted from the entire surface profile. For this example of FIGS. 3A and 3B, the outer region 23 has a lower power than the center region, and the center region 21 has higher curvature than the outer region. These simplified surfaces as shown in FIGS. 3A and 3B are used to generate images (see FIGS. 5 and 6) in a multifocal lens simulator according to embodiments. The shapes of the regions of the multifocal lens 20 will be described in more detail below.

Referring to FIGS. 1, 3A and 3B, the multifocal lens 20 may be a multifocal ophthalmic lens, e.g., a multifocal contact lens. The multifocal lens 20 can be formed of any suitable biocompatible material. Some examples of such materials include, without limitation, a non-ionic lens material, e.g., Hioxifilcon D. Hioxifilcon D is a copolymer of 2-hydroxyethyl methacrylate (2-HEMA) and 2,3-Dihydroxypropyl Methacrylate (Glycerol Methacrylate, GMA) and cross-linked with ethylene glycol dimethacrylate (EGDMA). The multifocal lens 20 may include 46% Hioxifilcon D and 54% water by weight when immersed in normal saline solution buffered with sodium borate. The lens is available in a blue visibility-handling tint, phthalocyanato (2)-(copper).

The multifocal lens 20 may have a center-near design, where the power of the lens is higher at the center to provide near vision, or a center-distance design where the center of the lens has a lower power for distance vision. The difference in power of the center region and outer region may be specified as the "add power" (e.g., in the unit of diopter). The inner boundary of the outer region 23 may be determined by the outer boundary of the intermediate region 22, which is shaped differently to either of the other two regions. The diameter of the center region 21, and the diameter of the intermediate region 22 can be adjusted as design variables.

With the center-near design, for example, the multifocal lens 20 may have the intermediate region 22 between the outer region 23 and the center region 21. The intermediate region 22 may have an annular region defined physically on the multifocal lens 20. The annular region may have a circular arc cut or defined in a manner that blends tangentially with both the inner region (e.g., center region) and the outer region 23. The circular arc may be a portion of an off-axis circle that does not have its center on an optical axis OA of the multifocal lens 20 (see FIG. 1), so that the annular region does not have a simple spherical power. When the radius of curvature R1 of the center region 21 is subtracted from the surface of the multifocal lens 20, the rest of the lens surface becomes flatter and the intermediate region 22 may curve in the opposite direction towards the outer region 23 (see FIG. 3A). Similarly, when the radius of curvature R3 of the outer region 23 is subtracted from the surface of the multifocal lens 20, the rest of the lens surface becomes flatter and the intermediate region 22 may curve in the opposite direction (see FIG. 3B).

On the other hand, with the center-distance design, the surface curvatures are swapped. That is, the center region 21 has a lower power than the intermediate and outer regions, and the outer region 23 has higher curvature than the intermediate and center regions. With the center-distance design, the outer region 23 may have a particular amount of "add power" by setting up a physical lens in the outer region 23. With the center-distance design, the multifocal lens 20 may have an intermediate region 22 between the outer region 23 and the center region 21. The intermediate region 22 may have an annular region defined physically on the multifocal lens 20. The annular region may have a circular arc cut or defined in a manner that blends tangentially with both the inner region (e.g., center region) and the outer region 23. The circular arc may be a portion of an off-axis circle that does not have its center on an optical axis OA of the multifocal lens 20 (see FIG. 1), so that the annular region does not have a conventional spherical power.

The intermediate region 22 may have a cross-section whose shape is similar to a section of an "ogive" arch shape. The ogive of the intermediate region 22 may have a portion of a circle whose center is not on the optical axis (see FIG. 1).

Figure 4:
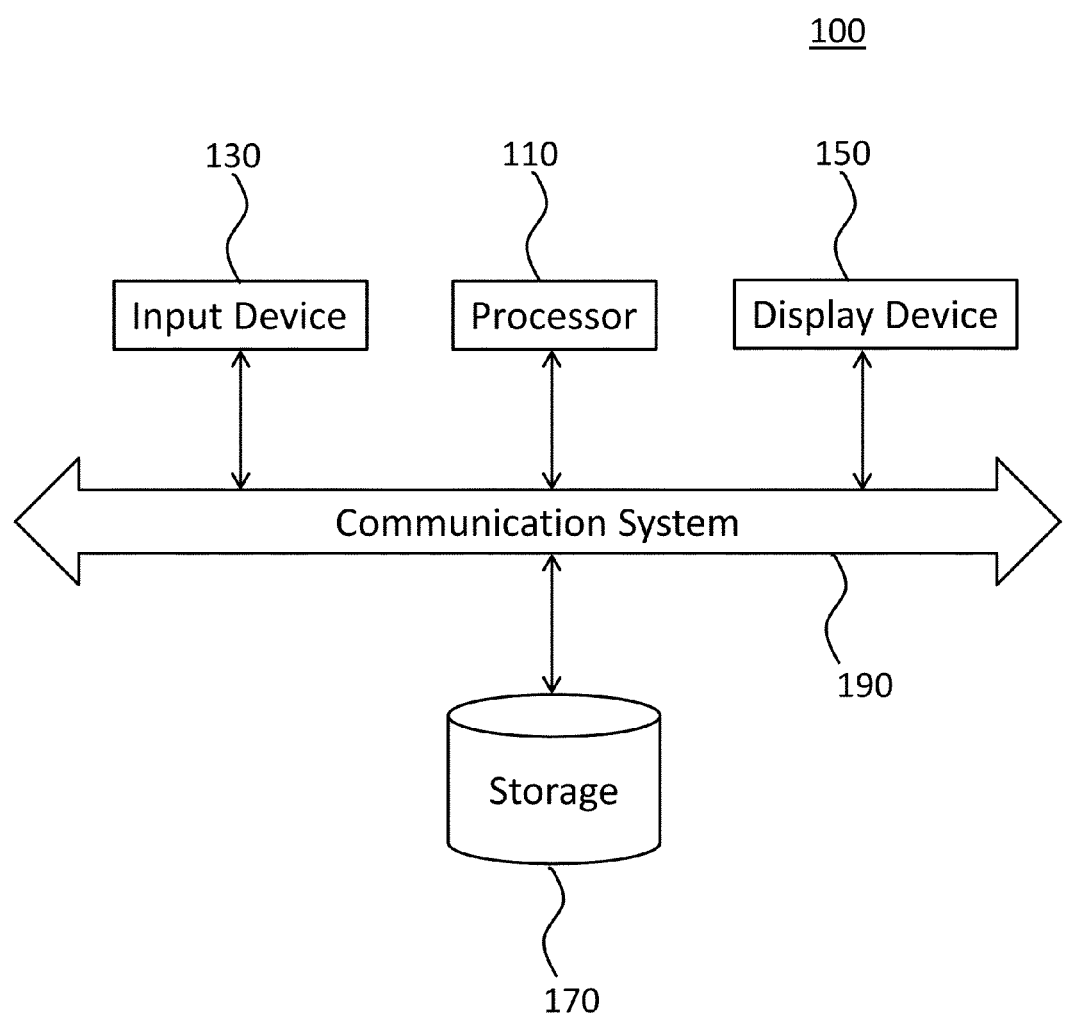
FIG. 4 is a block diagram of a multifocal lens simulator.

FIG. 4 is a block diagram of a multifocal lens simulator 100 in accordance with another embodiment. Referring to FIG. 4, the multifocal lens simulator 100 may include a processor 110, an input device 130, a display device 150, a communication system 170 and a storage 190. The processor 110 may include a microprocessor, a central processing unit (CPU), a graphic processing unit (GPU) or the like.

The input device 130 may include a control panel, a track ball, a mouse, a keyboard or the like for receiving input from users. The input device 130 may also include a device to measure aberration of an eye, e.g., a Shack-Hartmann sensor, so that the measured aberration is inputted to an eye model.

The display device 150 may include a liquid-crystal display (LCD), a plasma display, a cathode ray tube (CRT), a projector, a printer, and the like, or other display devices for displaying two-dimensional images or three-dimensional representations.

The storage 170 may include at least one computer readable medium or memory programmed for storing data. The term "computer readable medium" as used herein refers to any medium that can store instructions and provide them to the processor 110 for execution. A computer readable medium may be non-volatile media and volatile media. Non-volatile media may include, for example, optical, magnetic disks, and magneto-optical disks. Volatile media may include dynamic memory, such as main memory. Computer readable media may include, for example, hard disks, floppy disks, tape, magneto-optical disks, PROMs (EPROM, EEPROM, Flash EPROM), DRAM, SRAM, SDRAM, or any other magnetic medium, compact disks (e.g., CD-ROM), and the like.

The communication system 190 may include transmission media, for example, wire, coaxial cables, fiber optics, USB, RS-232, a controller area network, PCMCIA, serial buses, parallel buses and the like, constituting a data bus for transferring data among the processor 110, the input device 130, the display device 150, the storage 190, and external servers or devices.

Figure 5:
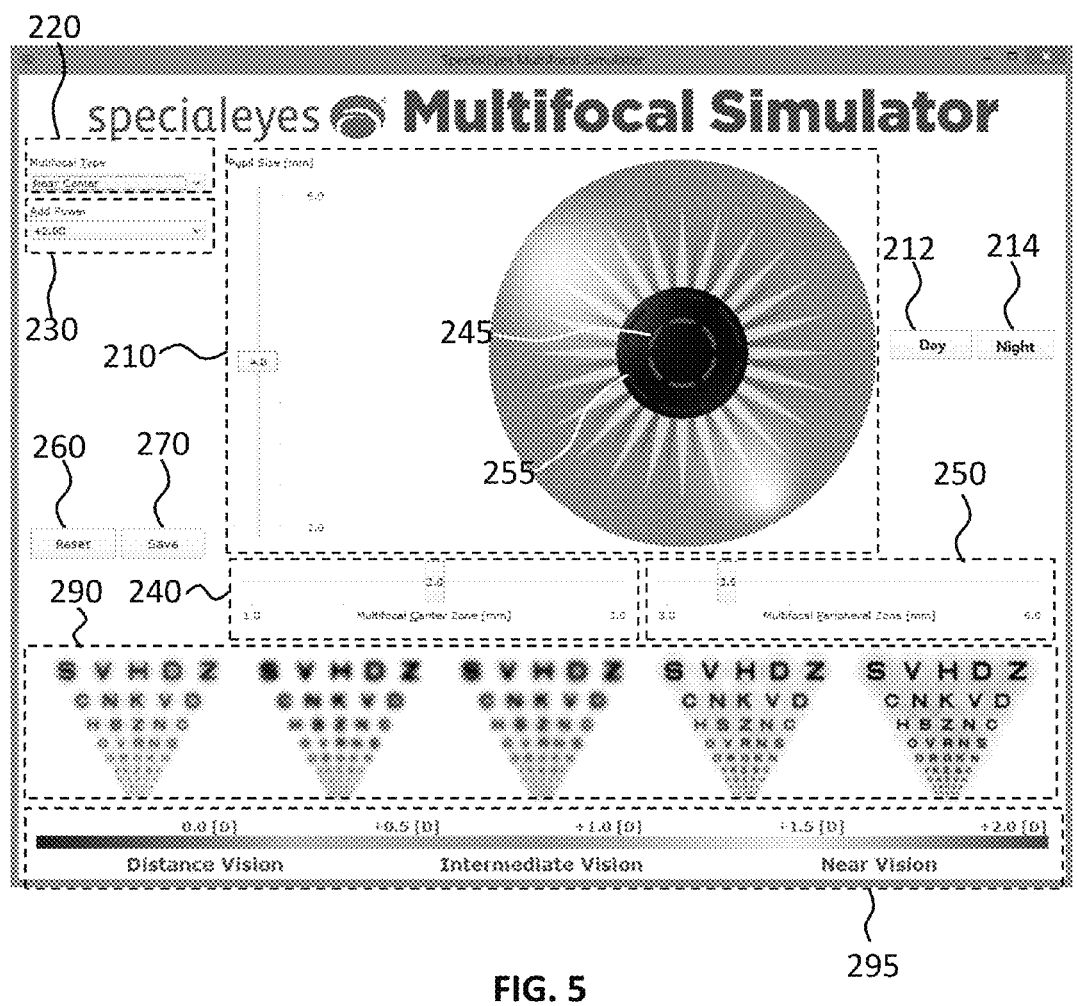
FIG. 5 is an exemplary display of a multifocal lens simulator in accordance with another embodiment.

FIG. 5 is an exemplary display 200 of a multifocal lens simulator. The display 200 may be displayed in the display device 150 and include a plurality of graphical user interfaces (GUIs) and a plurality of objects including simulated images 290. Each simulated image may be displayed by selecting the patient's pupil size coupled together with refractive add power, chosen multifocal design type, center zone size, and peripheral zone size settings.

The input device 130 (see FIG. 4) may be configured to input information on a pupil of an eye of the patient. The pupil information may include a diameter of the pupil. The display 200 may include input controls 210 for inputting a pupil size or a diameter of the pupil in a predetermined unit (e.g., mm) by the input device 130. The input controls 210 may include a vertical slider together with an image of the pupil having the inputted pupil size so that the pupil image is updated any time the inputted pupil size changes. However, the input controls 210 are not limited to those shown and may include buttons, horizontal sliders, a list box, a drop-down list, an input text box and the like.

Referring to FIG. 5, the inputted pupil size may be adjusted based on an illumination or light level in a room where the pupil information is measured. For example, when the user press a 'day' button 212 after a pupil size is inputted, the inputted pupil size may be adjusted (and the pupil image updated accordingly) based on an average amount of pupil contraction or dilation in a daytime room setting or under a regular illumination. On the other hand, when the user press a 'night' button 214 after a pupil size is inputted, the inputted pupil size may be adjusted (and the pupil image updated accordingly) based on an average amount of pupil contraction or dilation in a nighttime room setting or a dark illumination. Such illumination buttons according to the present inventive concept are not limited to the 'day' button and the 'night' button. For example, the display 200 may include an 'indoor' button and an 'outdoor' button.

The input device 130 (see FIG. 4) may be configured to input design information for a multifocal lens. The design information for a multifocal lens may include types of specific lens designs (e.g., the center-near design and the center-distance design as described above), refractive add power, and physical dimensions of regions (or zones) of the multifocal lens.

The design information for a multifocal lens may include a multifocal lens design selected among different types of specific designs, e.g., the center-near design and the center-distance design as described above. Referring to FIG. 5, the display 200 may include input controls 220 for selecting a type of multifocal lens design, for example, among the center-near design and the center-distance design, by the input device 130. However, the input controls 220 are not limited to those shown and may include buttons, sliders, an input text box, and the like.

The design information for a multifocal lens may also include the refractive add power of the multifocal lens to be applied to either the center region 21 (in the center-near design) or the outer region 23 (in the center-distance design). Referring to FIG. 5, the display 200 may include input controls 230 for inputting refractive add power of the multifocal lens in a predetermined unit (e.g., diopter or D) by the input device 130. The input controls 230 may include a drop-down list. However, the input controls 230 according to the present inventive concept are not limited to those shown and may include a list box, an input text box, a radio button, and the like.

The design information for a multifocal lens may also include physical dimensions of regions (or zones) of the multifocal lens. As described above, referring to FIG. 1, the regions of the multifocal lens 20 may include the center region 21 (or zone) with the radius of curvature R1, the intermediate region 22 (or zone) with the radius of curvature R2, and the outer region 23 (or peripheral zone) with the radius of curvature R3.

Referring to FIG. 5, the display 200 may include input controls 240 for inputting a physical dimension of the center region 21 of the multifocal lens 20 in a predetermined unit (e.g., mm). FIG. 5 shows that the input controls 240 include a horizontal slider only. However, the input controls 240 are not limited to those shown and may include a vertical slider, buttons, a list box, a drop-down box, an input text box and the like. The display 200 may also include input controls 250 for inputting a physical dimension of the outer region 23 of the multifocal lens 20 in a predetermined unit (e.g., mm). FIG. 5 shows that the input controls 250 include a horizontal slider only. However, the input controls 250 are not limited to those shown and may include a vertical slider, buttons, a list box, a drop-down box, an input text box and the like.

Referring to FIG. 5, the inputted dimension of the center region 21 may be graphically indicated on the pupil image. For example, when the user inputs a dimension of the center region 21 using the input control 240 by the input device 130, a circle 245 indicating the inputted dimension of the center region 21 may be rendered on the pupil image. Similarly, the inputted dimension of the outer region 23 may be graphically indicated on the pupil image. For example, when the user inputs a dimension of the outer region 23 using the input control 250 by the input device 130, a circle 255 may be rendered on the pupil image so that the region outside the circle 255 indicates the inputted dimension of the outer region 23.

The multifocal lens simulator preferably generates images that simulate distance, intermediate, and near vision across a specified add power range. Referring to FIG. 5, the display 200 may include a simulated image or a plurality of simulated images 290 that are visible to the eye of the patient when the multifocal lens 20 is disposed in the eye. The processor 110 (see FIG. 4) may be configured to generate, based on the inputted pupil information and design information, the simulated images 290. The simulated images 290 may be monochromatic. Each of the simulated images 290 may be a chart image used to measure visual acuity but the present inventive concept is not limited thereto. FIG. 5 shows five simulated images 290 including a first simulated image (e.g., the leftmost image in the images 290) relating to a first defocus value indicating distance vision of the eye, a second simulated image (e.g., the third leftmost image in the images 290) relating to a second defocus value indicating intermediate vision of the eye, and a third simulated image (e.g., the rightmost image in the images 290) relating to a third defocus value indicating near vision of the eye. Referring to FIG. 5, the display 200 may display the first, second and third simulated images side by side, however, the present inventive concept is not limited thereto. For example, the first, second and third simulated images may be displayed in separate sections of a display. Referring to FIG. 5, the display 200 may also display labels and diopter values 295, corresponding to the first, second and third simulated images.

The displayed simulated image may change any time one of the above mentioned settings is manipulated. For example, referring to FIG. 5, the display 200 may be configured to update the displayed simulated images 290 any time a change is made in one of the input controls 210, 220, 230, 240 and 250, which correspond to the input parameters of a pupil size, a selected type of multifocal lens design, refractive add power, a dimension of the center zone, a dimension of the peripheral zone, respectively. This may be performed in two ways. First, the processor 110 calculates all the images corresponding to possible sets of values of the input parameters (e.g., possible values in combinations of predetermined ranges of the respective input parameters) beforehand; and immediately after a set of values of the input parameters is inputted by the input device 130, the processor 110 looks up all the pre-calculated images and the display 200 displays the images 290 corresponding to the inputted set of values of the input parameters, among the all the pre-calculated images. Second, immediately after a set of values of the input parameters is inputted by the input device 130, the processor 110 calculates images corresponding to the inputted set of values of the input parameters. Moreover, the displayed simulated image may change to predetermined default images when a reset button 260 is pressed. This interactive aspect of the present inventive concept is valuable because a lot of information that cannot be conveniently reduced down to a single number is displayed. The user can potentially make judgments about small nuances that are visible simultaneously in different regions of the multiple images.

Figure 6:
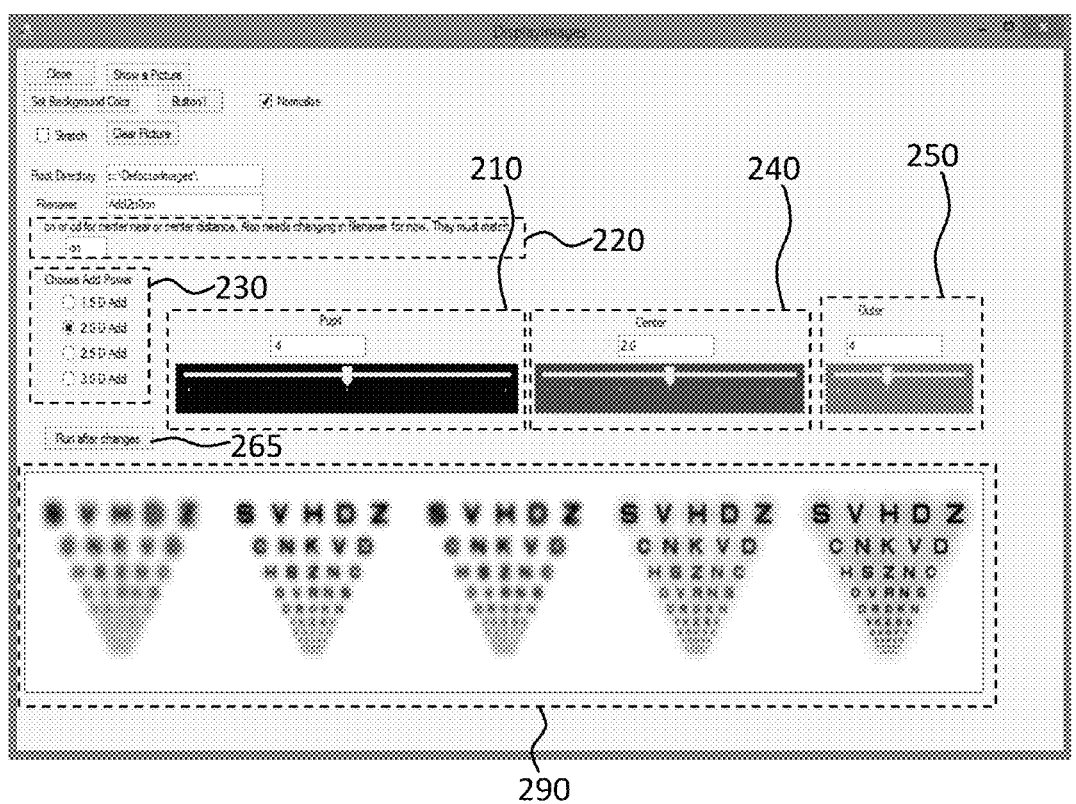
FIG. 6 is another exemplary display of a multifocal lens simulator.

FIG. 6 is another exemplary display 200' of a multifocal lens simulator. The display 200' may be displayed in the display device 150 (see FIG. 4) and include a plurality of graphical user interfaces (GUIs) and a plurality of objects including simulated images 290. Each simulated image may be displayed by selecting the patient's pupil size and refractive add power coupled together with chosen multifocal design type, center zone size, and peripheral zone size settings.

The input device 130 (see FIG. 4) may be configured to input information on a pupil of an eye of the patient. The pupil information may include a diameter of the pupil. Referring to FIG. 6, the display 200' may include input controls 210 for inputting a pupil size or a diameter of the pupil in a predetermined unit (e.g., mm) by the input device 130. FIG. 6 shows that the input controls 210 include a horizontal slider together with an input text box. However, the input controls 210 according to the present inventive concept are not limited to those shown and may include buttons, vertical sliders, a list box, a drop-down list and the like.

The design information for a multifocal lens may include a multifocal lens design selected among different types of specific designs, e.g., the center-near design and the center-distance design as described above. Referring to FIG. 6, the display 200' may include input controls 220 for selecting a type of multifocal lens design, for example, among the center-near design and the center-distance design, by the input device 130. The input controls 220 may include an input text box. However, the input controls 220 according to the present inventive concept are not limited to those shown and may include a drop-down list, buttons, sliders, and the like.

The design information for a multifocal lens may also include the refractive add power of the multifocal lens to be applied to either the center region 21 (in the center-near design) or the outer region 23 (in the center-distance design). Referring to FIG. 6, the display 200' may include input controls 230 for inputting refractive add power of the multifocal lens in a predetermined unit (e.g., diopter or D) by the input device 130. The input controls 230 may include a radio button. However, the input controls 230 according to the present inventive concept are not limited thereto and may include a drop-down list, a list box, an input text box and the like.

Referring to FIG. 6, the display 200' may include input controls 240 for inputting a physical dimension of the center region 21 of the multifocal lens 20 in a predetermined unit (e.g., mm). FIG. 6 shows that the input controls 240 include a horizontal slider together with an input text box. However, the input controls 240 are not limited to those shown and may include a vertical slider, buttons, a list box, a drop-down box and the like. The display 200' may also include input controls 250 for inputting a physical dimension of the outer region 23 of the multifocal lens 20 in a predetermined unit (e.g., mm). FIG. 6 shows that the input controls 250 include a horizontal slider together with an input text box. However, the input controls 250 are not limited to those shown and may include a vertical slider, buttons, a list box, a drop-down box and the like.

The multifocal lens simulator preferably generates images that simulate distance, intermediate, and near vision across a specified add power range. Referring to FIG. 6, the display 200' may include a simulated image or a plurality of simulated images 290 that are visible to the eye of the patient when the multifocal lens 20 is disposed in the eye. The processor 110 (see FIG. 4) may be configured to generate, based on the inputted pupil information and design information, the simulated images 290. The simulated images 290 may be monochromatic. Each of the simulated images 290 may be a chart image used to measure visual acuity but the present inventive concept is not limited thereto. FIG. 6 shows five simulated images 290 including a first simulated image (e.g., the leftmost image in the images 290) relating to a first defocus value indicating distance vision of the eye, a second simulated image (e.g., the third leftmost image in the images 290) relating to a second defocus value indicating intermediate vision of the eye, and a third simulated image (e.g., the rightmost image in the images 290) relating to a third defocus value indicating near vision of the eye. Referring to FIG. 6, the display 200' may display the first, second and third simulated images side by side, however, the present inventive concept is not limited thereto. For example, the first, second and third simulated images may be displayed in separate sections of a display.

After the above-mentioned settings are manipulated, the displayed simulated image may change according to the settings when a run or display button is pressed. For example, referring to FIG. 6, after a change is made in at least one of the input controls 210, 220, 230, 240 and 250, which correspond to a pupil size, a selected type of multifocal lens design, refractive add power, a dimension of the center zone, a dimension of the peripheral zone, respectively, the display 200' may be configured to update the displayed simulated images 290 when a 'run after changes' button 265 is pressed.

Figure 7:
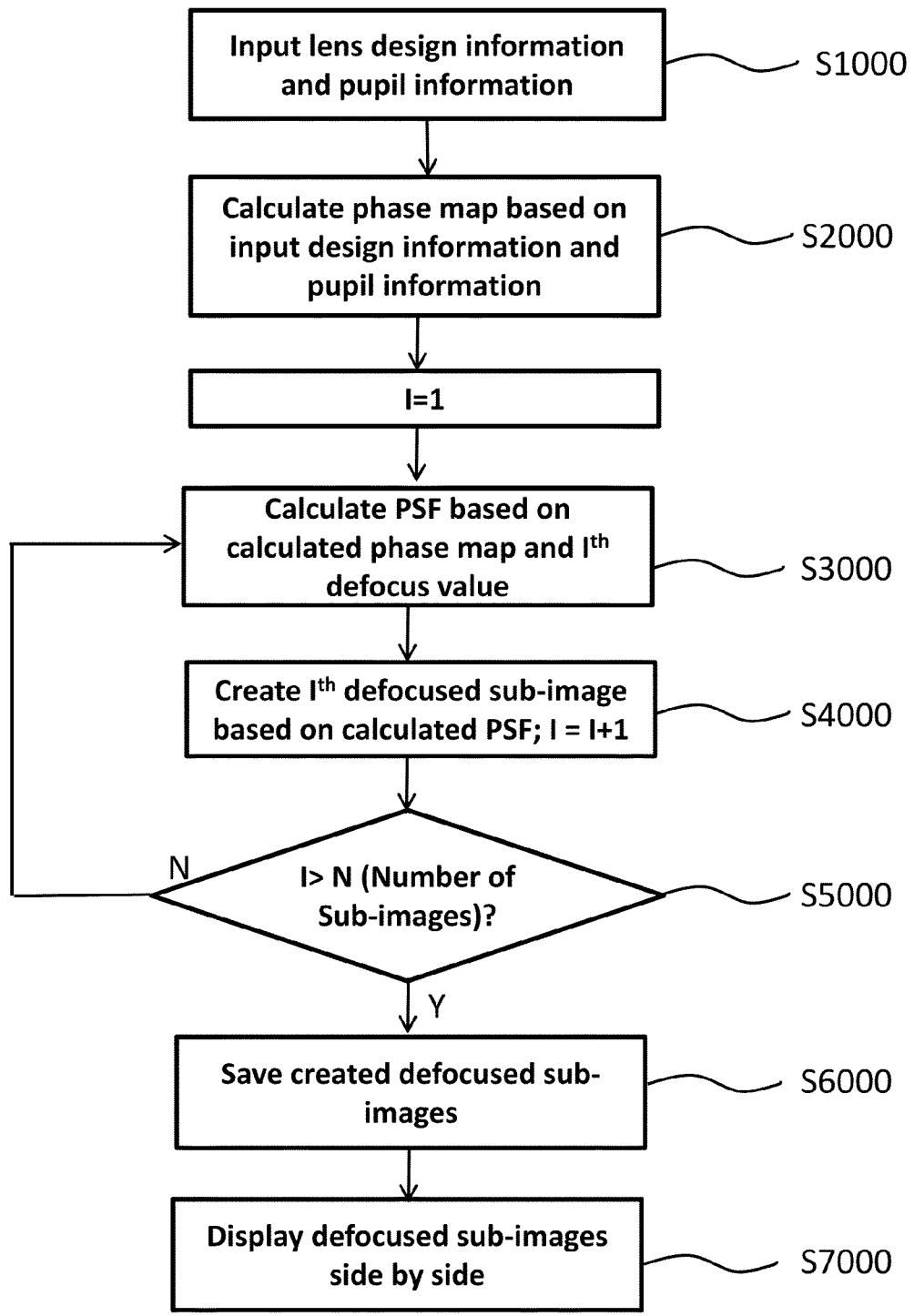
FIG. 7 is a flowchart showing a method of generating and displaying simulated images in a multifocal lens simulator.

FIG. 7 is a flowchart showing a method of generating and displaying simulated images in a multifocal lens simulator of FIGS. 4-6. This method allows the user to see the defocus effects of the design and pupil variables, and to interactively change them to see how they change the image quality. This interactive aspect of the present inventive concept is valuable because a lot of information that cannot be conveniently reduced down to a single number is displayed. The user can potentially make judgments about small nuances that are visible simultaneously in different regions of the multiple images.

In step S1000, information on a pupil of an eye and design information for a multifocal lens may be inputted from the display 200 or 200' by the input device 130. The pupil information may include a diameter of the pupil. The design information for a multifocal lens may include types of specific lens designs (e.g., the center-near design and the center-distance design as described above), refractive add power, and physical dimensions of regions (or zones) of the multifocal lens. For example, referring to FIGS. 5 and 6, add power, a lens design type, a dimension of the center region 21 and a dimension of the outer region 23 may be inputted from the input controls 230, the input controls 220, the input controls 240 and the input controls 250, respectively.

In step S2000, a phase map for the eye may be calculated. For example, a multifocal phase map may be calculated based on the inputted design information for the multifocal lens 20 including the multifocal component 50, the defocus component 60 and the aberration component 70 (see FIG. 2B). For example, defocus is added as an additional phase function to simulate the effect of an eye viewing an object at different distances, and is included in the phase map as a particular defocus value. In the embodiment of FIGS. 5 and 6, different defocus values corresponding to the number (N) of simulated sub-images 290 are calculated. This phase map calculation step will be described in more detail in the following sections with reference to FIGS. 8-10.

Referring to FIG. 7, in step S3000, after calculating the phase map and an $i^{th}$ particular defocus value (i≤N), a point spread function (PSF) may be calculated using a Fast Fourier Transform (FFT). In step S4000, a simulated image (e.g., images 290 in FIGS. 5 and 6) that is visible to the eye when the multifocal lens is disposed in the eye may be generated by the processor 110 based on the inputted pupil information and design information. More particularly, a simulated image relating to the particular defocus value may be generated based on the PSF calculated in step S3000. For example, the simulated image may be generated by convolving the PSF with the original chart image. The convolution of the PSF with the original image may also be performed using an FFT calculation method.

The simulated image generation step 4000 may be repeated until it is determined in step S5000 that a predetermined number of simulated images having respective defocus values, called sub-images, have been created. The created sub-images may include a first simulated image relating to a first defocus value indicating distance vision of the eye, a second simulated image relating to a second defocus value indicating intermediate vision of the eye, and a third simulated image relating to a third defocus value indicating near vision of the eye, as shown in FIGS. 5 and 6.

In step S6000, the created defocused sub-images may be saved in a storage, for example, the storage 170 (see FIG. 4). Alternatively, the saving of the created defocused sub-images is not automatically performed but may be performed when the user presses a save button 270 (see FIG. 5). In step S7000, the defocused sub-images generated by the processor 110 may be displayed by the display device 150. For example, the defocused sub-images may be displayed as the images 290 in FIGS. 5 and 6. In displaying the defocused sub-images, the first simulated image relating to the first defocus value indicating distance vision of the eye, the second simulated image relating to the second defocus value indicating intermediate vision of the eye, and the third simulated image relating to a third defocus value indicating near vision of the eye may be displayed side by side, as shown in FIGS. 5 and 6.

Figure 8:
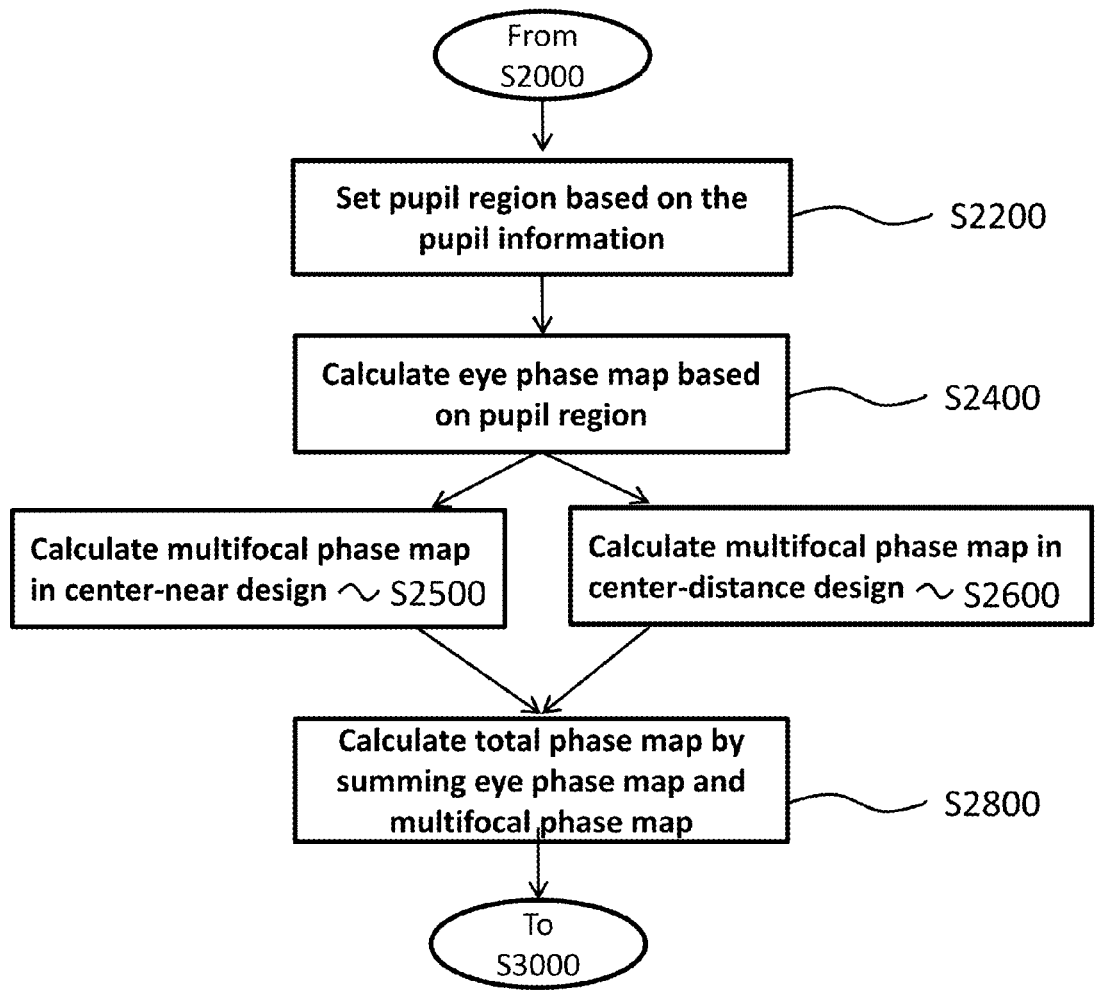
FIG. 8 is a flowchart showing a procedure of calculating phase maps in a multifocal lens simulator.

FIG. 8 is a flowchart showing a procedure of calculating phase maps in a multifocal lens simulator.

Referring to FIG. 8, in step S2200, a pupil region may be set based on the inputted pupil information, e.g., a diameter of the pupil. The processor 110 (see FIG. 4) may use a data structure like a two-dimensional array to represent a phase map and set the pupil region thereon. For example, pixels in an outer region of the phase map may be obscured based on a pupil region.

Referring to FIG. 8, in step S2400, an eye phase map may be calculated. In the eye phase map calculation, an aberration phase map may be calculated by generating a wavefront based on the eye model and then adding aberration of the eye in the form of Zernike polynomials to the generated wavefront. The aberration phase map may also be obtained by measuring the aberration of the eye from the eye by a Shack-Hartmann sensor. According to another embodiment, the eye phase map may be calculated by measuring a wavefront from the eye using various methods including corneal topography.

After calculating the eye phase map in step S2400, the multifocal phase map in the multifocal lens may be calculated or reconstructed from the wavefront measured from the multifocal component 50 (see FIG. 2B) based on the design information including types of specific lens designs (e.g., the center-near design and the center-distance design as described above), refractive add power, and physical dimensions of the three regions of the multifocal lens 20. Alternatively, the calculation of the multifocal phase map in the multifocal lens 20 may be performed before performing step S2400. If the lens design type is the center-near design, the multifocal phase map in the multifocal lens 20 may be calculated in step S2500 (see also FIG. 9). If the lens design type is the center-distance design, the multifocal phase map may be calculated in step S2600 (see also FIG. 10). The detailed methods for the calculation of the multifocal phase map will be described in the following sections with reference to FIGS. 9 and 10.

Referring to FIG. 8, after calculating the eye phase map and the multifocal phase map, in step S2800, a total phase map may be calculated by summing the eye phase map and the multifocal phase map.

Figure 9:
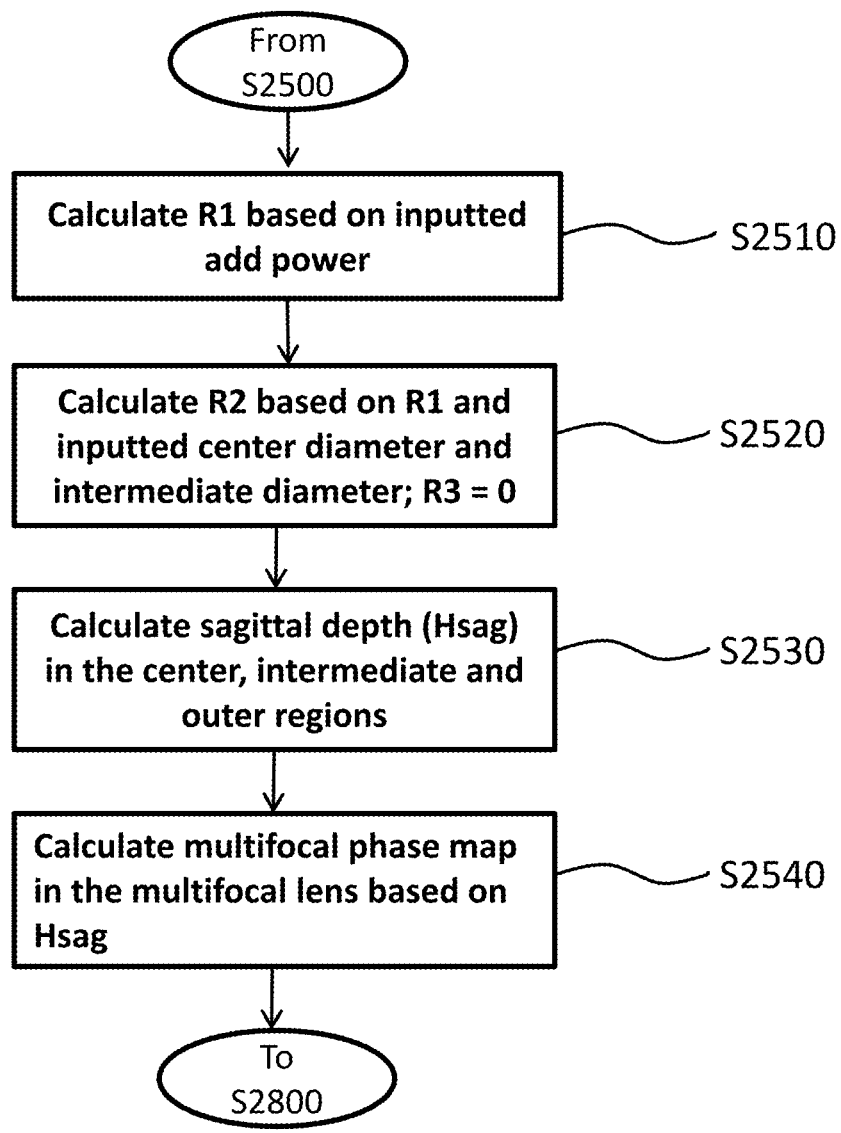
FIG. 9 is a flowchart showing a procedure of calculating a multifocal phase map based on a center-near design of a multifocal lens in a multifocal lens simulator.

FIG. 9 is a flowchart showing a procedure of calculating a multifocal phase map based on a center-near design of a multifocal lens in a multifocal lens simulator, by creating a simulated multifocal component.

Referring to FIG. 9, in step 2510, the radius of curvature R1 of the center region 21 of a simulated multifocal component may be calculated by the processor 110 (see FIG. 4) based on the add power in diopters (denoted by "Add_power") inputted from the input controls 220 (see FIGS. 5 and 6). The radius R1 in mm may be calculated using the following Equation 1.

$$R1=(n2-n1)*1000/\text{Add\_power} \qquad \text{(Equation 1)}$$

In the Equation 1, "n2" denotes a refractive index of lens material; and "n1" denotes refractive index of the surrounding material. The difference between the two index values of n2 and n1 is used to define a physical lens with a certain power.

In step S2520, the radius of curvature R2 of the intermediate region 22 may be calculated by the processor 110 (see FIG. 4) based on a diameter of the center region 21 (denoted by "2*Rcent"), e.g., that inputted from the input controls 240, and a diameter of the intermediate region (denoted by "2*Rasph"), e.g., that inputted from the input controls 240 and 250; and the radius R3 of curvature of the outer region 23 may be set to zero. The radius R2 may be calculated using the following Equation 2.

$$R2=-(\text{Rasph}-\text{Rcent})*R1/\text{Rcent} \quad \text{(Equation 2)}$$

In step 2530, after setting the center region 21 based on Rcent by the processor 110 (see FIG. 4), a sagittal depth of the multifocal lens (denoted by "Hsag") may be calculated in the center region 21. The sagittal depth Hsag is defined as the distance from a flat plane at a given diameter to the highest point (or apex) of a concave surface of the lens. Hsag in the center region 21 may be calculated based on R1 for each of points in the center region 21 at a radial distance p from the optical axis OA using the following Equation 3.

$$\text{Hsag}=p^2/2/R1 \quad \text{(Equation 3)}$$

In step 2530, after setting the intermediate region 22 based on Rcent and Rasph by the processor 110 (see FIG. 4), Hsag may be calculated in the intermediate region 22. Hsag in the intermediate region 22 may be calculated based on R2, Rcent and Rasph for each of points in the intermediate region 22 at a radial distance p from the optical axis OA using the following Equation 4.

$$\text{Hsag}=(\text{Rcent}^2/2/R1)-(\text{Rasph}-\text{Rcent})^2/2/R2+(\text{Rasph}-p)^2/2/R2 \quad \text{(Equation 4)}$$

In step 2530, after setting the outer region 23 based on Rasph by the processor 110 (see FIG. 4), Hsag may be calculated in the outer region 23. Hsag in the outer region 23 may be calculated based on R2, Rcent and Rasph using the following Equation 5.

$$\text{Hsag}=(\text{Rcent}^2/2/R1)-(\text{Rasph}-\text{Rcent})^2/2/R2 \quad \text{(Equation 5)}$$

In step 2540, a multifocal phase map (denoted by "$M_{mf}$") in the multifocal lens with the center-near design may be calculated. $M_{mf}$ may be calculated in μm based on Hsag values in the respective center, intermediate and outer regions using the following Equation 6.

$$M_{mf}=1000*(n1*\text{Hsag}+n2*(-\text{Hsag})) \quad \text{(Equation 6)}$$

Figure 10:
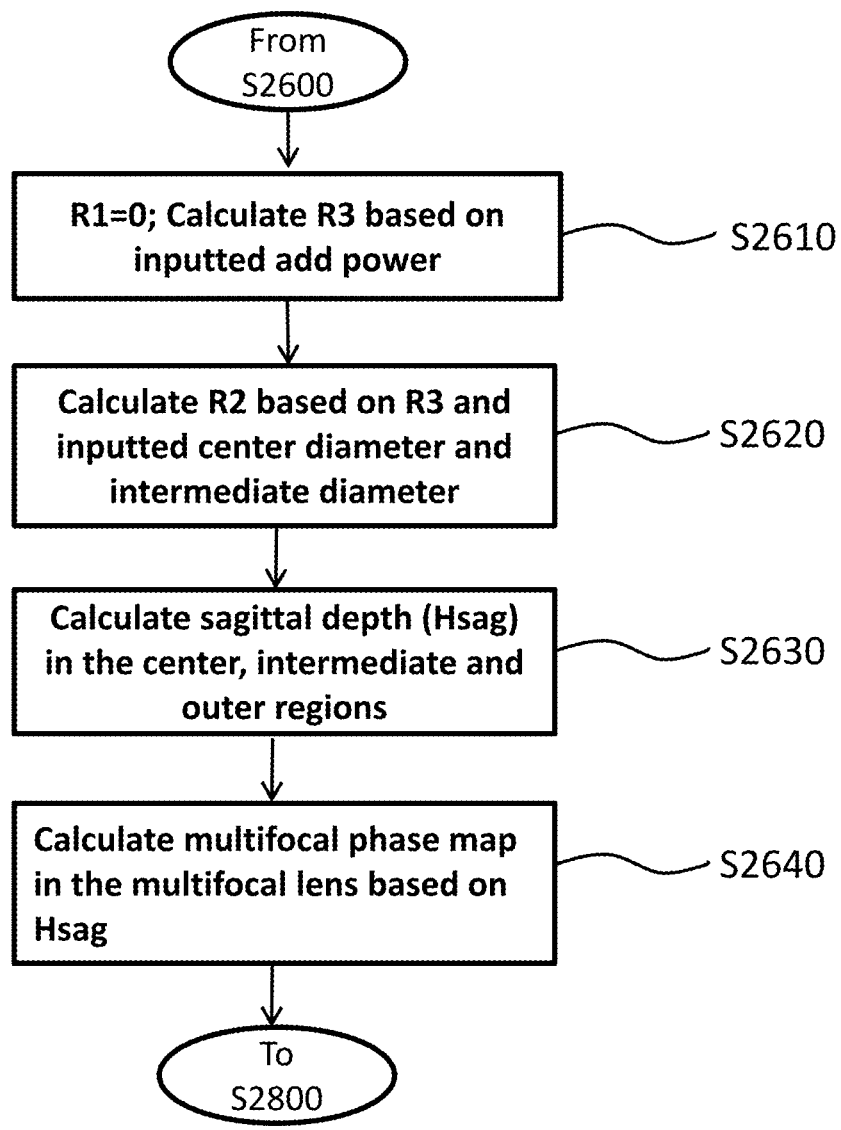
FIG. 10 is a flowchart showing a procedure of calculating a multifocal phase map based on a center-distance design of a multifocal lens in a multifocal lens simulator.

FIG. 10 is a flowchart showing a procedure of calculating a multifocal phase map based on a center-distance design of a multifocal lens in a multifocal lens simulator. With the center-distance design, for example, the radius of curvature R3 of the outer region 23 may be greater than zero, i.e., the outer region 23 is curved; and the radius of curvature R1 of the center region 21 may be infinity, i.e., the center region 21 is flat.

Referring to FIG. 10, in step 2610, the radius of curvature R3 of the outer region 23 may be calculated by the processor 110 (see FIG. 4) based on the add power (denoted by "Add_power") inputted from the input controls 220 (see FIGS. 5 and 6); and the radius of curvature R1 of the center region 21 may be set to infinity. The radius R3 may be calculated using the following Equation 7.

$$R3=(n2-n1)*1000/\text{Add\_power} \quad \text{(Equation 7)}$$

In step S2620, the radius of curvature R2 of the intermediate region 22 may be calculated by the processor 110 (see FIG. 4) based on R3, a diameter of the center region 21 (denoted by "2*Rcent"), e.g., that inputted from the input controls, and a diameter of the intermediate region 22 (denoted by "2*Rasph"). The radius R2 may be calculated using the following Equation 8.

$$R2=-(\text{Rasph}-\text{Rcent})*R3/\text{Rasph} \quad \text{(Equation 8)}$$

In step 2630, after setting the center region 21 based on Rcent by the processor 110 (see FIG. 4), a sagittal depth of the multifocal lens (denoted by "Hsag") may be set to zero in the center region 21.

In step 2630, after setting the intermediate region 22 based on Rcent and Rasph by the processor 110 (see FIG. 4), Hsag may be calculated in the intermediate region 22. Hsag in the intermediate region 22 may be calculated based on R2 and Rcent for each of points in the intermediate region 22 at a radial distance p from the optical axis OA using the following Equation 9.

$$\text{Hsag}=(p-\text{Rcent})^2/2/R2 \quad \text{(Equation 9)}$$

In step 2630, after setting the outer region 23 based on Rasph by the processor 110 (see FIG. 4), Hsag may be calculated in the outer region 23. Hsag in the outer region 23 may be calculated based on R2, R3 and Rasph for each of points in the outer region 23 at a radial distance p from the optical axis OA using the following Equation 10.

$$\text{Hsag}=(\text{Rasph}^2/2/R3)*(R2/R3-1)+p^2/2/R3 \quad \text{(Equation 10)}$$

In step 2640, a multifocal phase map (denoted by "$M_{mf}$") in the multifocal lens with the center-distance design may be calculated. $M_{mf}$ may be calculated in μm based on Hsag values in the respective center, intermediate and outer regions using the above-noted Equation 6.

As set forth above, the multifocal contact lens according to embodiments may include a center region, an outer region, and an intermediate region that is disposed therebetween and has an annular region.

Moreover, according to exemplary embodiments, the multifocal lens simulator may be configured to input information on a pupil of an eye of the patient, e.g., a diameter of the pupil, and design information for a multifocal lens, e.g., types of specific lens designs, refractive add power, and physical dimensions of regions of the multifocal lens. With the inputted pupil information and design information, the multifocal lens simulator may be configured to generate and display images that simulate near, intermediate, and distance vision across a specified add power range. Since the multifocal lens simulator utilizes various design variables based on the pupil information and design information to generate simulated images indicating near, intermediate, and distance vision, the multifocal lens simulator can achieve optimized simulated image contrast for both the near vision and distance vision.

Furthermore, since the multifocal lens simulator utilizes different design variables in different lens designs (e.g., the center-near design and the center-distance design as described above), the multifocal lens simulator can provide enhanced support for different types of multifocal lens designs.

Multifocal contact lenses and a simulator thereof according to embodiments utilize the combination of zonal contact lenses, adjustable design parameters, residual accommodation, pupil diameter information, simulated images at different distances presented side by side, and the ability to rapidly change the set of images, thereby optimizing clinical implementation of custom lenses for the individual patients.

While certain embodiments of the present invention have been shown and described, it will be apparent to those skilled in the art that modifications and variations can be made without departing from the spirit and scope of the invention as defined by the appended claims.

What is claimed is:

1. An apparatus for generating simulated images, comprising:

an input device configured to input information on a pupil of an eye and design information for a multifocal lens;

a processor configured to generate, based on the inputted pupil information and design information, a simulated image that is visible to the eye when the multifocal lens is disposed in the eye; and a display device configured to display the simulated image generated by the processor.

2. The apparatus of claim 1, wherein:

the simulated image includes a first simulated image relating to a first defocus value indicating distance vision of the eye, a second simulated image relating to a second defocus value indicating intermediate vision of the eye, and a third simulated image relating to a third defocus value indicating near vision of the eye, and the display device is configured to display the first, second and third simulated images side by side.

3. The apparatus of claim 1, wherein:

the pupil information includes a diameter of the pupil of the eye, and the design information includes at least one of add power and physical dimensions of regions of the multifocal lens.

4. The apparatus of claim 1, further comprising a means to input aberration to an eye model.

5. The apparatus of claim 1, wherein the multifocal lens is a contact lens.

6. The apparatus of claim 1, wherein the processor is further configured to:

input aberrations for the eye based on measured wavefront aberrations or aberrations estimated from a corneal topography;

calculate a total phase map by summing an eye phase map and a multifocal phase map in the multifocal lens;

calculate a point spread function (PSF) based on the total phase map and a particular defocus value; and generate a simulated image relating to the particular defocus value based on the calculated PSF.

7. The apparatus of claim 1, wherein the display device is further configured to update the simulated image after one of the information on the pupil and the design information changes.

8. The apparatus of claim 7, wherein:

the processor is further configured to generate a plurality of images corresponding to predetermined sets of values of input parameters relating to the pupil information and the design information, the input device is further configured to input a particular set of values of the input parameters, and when the particular set of values of the input parameters is inputted, the processor is configured to look up the plurality of images and the display is configured to update the simulated image by displaying an image, among the plurality of images, corresponding to the particular set of values of the input parameters.

9. The apparatus of claim 7, wherein:

the input device is further configured to input a particular set of values of input parameters relating to the pupil information and the design information, and when the particular set of values of the input parameters is inputted, the processor is configured to generate the simulated image corresponding to the particular set of values of the input parameters.

10. A method for generating simulated images, comprising steps of:

inputting, by an input device, information on a pupil of an eye and design information for a multifocal lens;

based on the inputted pupil information and design information, generating, by a processor, a simulated image that is visible to the eye when the multifocal lens is disposed in the eye; and displaying, by a display device, the simulated image generated by the processor.

11. The method of claim 10, wherein:

the step of generating the simulated image includes generating a first simulated image relating to a first defocus value indicating distance vision of the eye, a second simulated image relating to a second defocus value indicating intermediate vision of the eye, and a third simulated image relating to a third defocus value indicating near vision of the eye, and the step of displaying the simulated image includes displaying the first, second and third simulated images side by side.

12. The method of claim 10, wherein:

the pupil information includes a diameter of the pupil of the eye, and the design information includes at least one of add power and physical dimensions of regions of the multifocal lens.

13. The method of claim 10, wherein the multifocal lens is a contact lens.

14. The method of claim 10, wherein the step of generating the simulated image includes:

inputting aberrations for the eye based on measured wavefront aberrations or aberrations estimated from a corneal topography;

calculating a total phase map by summing an eye phase map and a multifocal phase map in the multifocal lens;

calculating a point spread function (PSF) based on the total phase map and a particular defocus value; and generating a simulated image relating to the particular defocus value based on the calculated PSF.

15. The method of claim 10, wherein the step of displaying the simulated image includes updating the simulated image after one of the information on the pupil and the design information changes.

16. The method of claim 15, wherein:

the step of generating the simulated image includes generating a plurality of images corresponding to predetermined sets of values of input parameters relating to the pupil information and the design information, the step of inputting information includes inputting a particular set of values of the input parameters, and the step of displaying the simulated image includes looking up, when the particular set of values of the input parameters is inputted, the plurality of images and updating the simulated image by displaying an image, among the plurality of images, corresponding to the particular set of values of the input parameters.

17. The method of claim 15, wherein:

the step of inputting information includes inputting a particular set of values of input parameters relating to the pupil information and the design information, and the step of generating the simulated image includes generating, when the particular set of values of the input parameters is inputted, the simulated image corresponding to the particular set of values of the input parameters.

18. A computer readable storage medium storing instructions that, when executed by a processor, cause the processor to perform operations for generating simulated images, the operations comprising steps of:

inputting, by an input device, information on a pupil of an eye and design information for a multifocal lens;

based on the inputted pupil information and design information, generating, by the processor, a simulated image that is visible to the eye when the multifocal lens is disposed in the eye; and displaying, by a display device, the simulated image generated by the processor.

19. The computer readable storage medium of claim 18, wherein:

the step of generating the simulated image includes generating a first simulated image relating to a first defocus value indicating distance vision of the eye, a second simulated image relating to a second defocus value indicating intermediate vision of the eye, and a third simulated image relating to a third defocus value indicating near vision of the eye, and the step of displaying the simulated image includes displaying the first, second and third simulated images side by side.

20. The computer readable storage medium of claim 18, wherein:

the pupil information includes a diameter of the pupil of the eye, and the design information includes at least one of add power and physical dimensions of regions of the multifocal lens.

21. The computer readable storage medium of claim 18, wherein the multifocal lens is a contact lens.

22. The computer readable storage medium of claim 18, wherein the step of generating the simulated image includes:

inputting aberrations for the eye based on measured wavefront aberrations or aberrations estimated from a corneal topography;

calculating a total phase map by summing an eye phase map and a multifocal phase map in the multifocal lens;

calculating a point spread function (PSF) based on the total phase map and a particular defocus value; and generating a simulated image relating to the particular defocus value based on the calculated PSF.

23. The computer readable storage medium of claim 18, wherein the step of displaying the simulated image includes updating the simulated image after one of the information on the pupil and the design information changes.

24. The computer readable storage medium of claim 23, wherein:

the step of generating the simulated image includes generating a plurality of images corresponding to predetermined sets of values of input parameters relating to the pupil information and the design information, the step of inputting information includes inputting a particular set of values of the input parameters, and the step of displaying the simulated image includes looking up, when the particular set of values of the input parameters is inputted, the plurality of images and updating the simulated image by displaying an image, among the plurality of images, corresponding to the particular set of values of the input parameters.

25. The computer readable storage medium of claim 23, wherein:

the step of inputting information includes inputting a particular set of values of input parameters relating to the pupil information and the design information, and the step of generating the simulated image includes generating, when the particular set of values of the input parameters is inputted, the simulated image corresponding to the particular set of values of the input parameters.

26. A multifocal lens, comprising a lens surface, the lens surface having:

a center region having a radius of curvature R1;

an outer region having a radius of curvature R3; and an intermediate region having a radius of curvature R2 and disposed between the center region and the outer region, wherein: the intermediate region has an annular region, the radius of curvature R2 is different from the radius of curvature R1 or the radius curvature R3, and the annular region has a circular arc that is a portion of an off-axis circle that does not have its center on an optical axis of the multifocal lens.

27. The multifocal lens of claim 26, wherein the circular arc blends tangentially with both the center region and the outer region.

28. A multifocal lens, comprising a lens surface, the lens surface having:

a center region having a radius of curvature R1;

an outer region having a radius of curvature R3; and an intermediate region having a radius of curvature R2 and disposed between the center region and the outer region, wherein: the intermediate region has an annular region, the radius of curvature R2 is different from the radius of curvature R1 or the radius curvature R3, and the multifocal lens is a contact lens.

* * * * *